US009798383B2

(12) United States Patent
Horesh

(10) Patent No.: US 9,798,383 B2
(45) Date of Patent: Oct. 24, 2017

(54) FACILITATING DYNAMIC EYE TORSION-BASED EYE TRACKING ON COMPUTING DEVICES

(71) Applicant: INTEL CORPORATION, Santa Clara, CA (US)

(72) Inventor: Nizan Horesh, Caesarea (IL)

(73) Assignee: INTEL CORPORATION, Santa Clara, CA (US)

( * ) Notice: Subject to any disclaimer, the term of this patent is extended or adjusted under 35 U.S.C. 154(b) by 6 days.

(21) Appl. No.: 14/491,680

(22) Filed: Sep. 19, 2014

(65) Prior Publication Data

US 2016/0085299 A1     Mar. 24, 2016

(51) Int. Cl.
 *G06F 3/01* (2006.01)
 *A61B 3/113* (2006.01)
 *A61B 3/00* (2006.01)
 *A61B 3/107* (2006.01)

(52) U.S. Cl.
 CPC ............ *G06F 3/013* (2013.01); *A61B 3/0025* (2013.01); *A61B 3/107* (2013.01); *A61B 3/113* (2013.01); *G06F 3/012* (2013.01)

(58) Field of Classification Search
 None
 See application file for complete search history.

(56) References Cited

U.S. PATENT DOCUMENTS

| | | | | |
|---|---|---|---|---|
| 5,280,312 A | * | 1/1994 | Yamada | G03B 13/02 351/200 |
| 2003/0098954 A1 | | 5/2003 | Amir et al. | |
| 2003/0123027 A1 | | 7/2003 | Amir et al. | |
| 2006/0110008 A1 | * | 5/2006 | Vertegaal | G06K 9/00604 382/103 |

(Continued)

FOREIGN PATENT DOCUMENTS

EP    2523069    11/2012

OTHER PUBLICATIONS

Pierrot-Deseillgny ("Effect of gravity on vertical eye position", NIH 2009) http://www.ncbi.nlm.nih.gov/pubmed/19645894.*

(Continued)

*Primary Examiner* — Patrick Edouard
*Assistant Examiner* — Matthew Yeung
(74) *Attorney, Agent, or Firm* — Blakely Sokoloff Taylor and Zafman LLP

(57) ABSTRACT

A mechanism is described for facilitating eye torsion-based accurate eye tracking on computing devices according to one embodiment. A method of embodiments, as described herein, includes determining a head pose representing a tilt of a head of a person in an image captured by a capturing device of one or more capturing/sensing device. The image may illustrate one or more eyes of the person. The method may further include estimating a gravity vector relating to an eye of the one or more eyes based on data relating to the image and sensed by a sensing device of the one or more capturing/sensing devices, computing a total torsion angle (Continued)

based on one or more of the head pose and the gravity vector, and estimating a gaze vector associated with eye to facilitate tracking of the eye. The tracking may include positions or movements of the eye based on the gaze vector.

24 Claims, 7 Drawing Sheets

(56) References Cited

U.S. PATENT DOCUMENTS

| | | |
|---|---|---|
| 2010/0110374 A1 | 5/2010 | Raguin et al. |
| 2012/0089049 A1* | 4/2012 | Suarez ............... A61B 5/11 600/558 |
| 2013/0222644 A1 | 8/2013 | Son et al. |
| 2014/0104575 A1* | 4/2014 | Zapala ............ A61B 5/1121 351/209 |
| 2014/0160438 A1* | 6/2014 | Wakil ................ A61B 3/107 351/246 |
| 2014/0211995 A1* | 7/2014 | Model ................ G06F 3/013 382/103 |
| 2014/0247232 A1* | 9/2014 | George-Svahn ........ G06F 3/02 345/173 |
| 2015/0077543 A1* | 3/2015 | Kerr ................. A61B 3/113 348/135 |

OTHER PUBLICATIONS

"Torsional and Vertical Eye Movements during Head Tilt Dynamic Characteristics", Pansell et al. IOVS, Jul. 2003.*

PCT/US2015/040768, "Notification of Transmittal of the International Search Report and the Written Opinion of the International Searching Authority, or the Declaration" mailed Nov. 2, 2015, pp. 13.

PCT International Preliminary Report on Patentability for counterpart PCT Application No. PCT/US2015/040768 issued Mar. 21, 2017, 9 pages.

* cited by examiner

FACILITATING DYNAMIC EYE TORSION-BASED EYE TRACKING ON COMPUTING DEVICES

FIELD

Embodiments described herein generally relate to computers. More particularly, embodiments relate to facilitating dynamic eye torsion-based eye tracking on computing devices.

BACKGROUND

With increasing use of computing devices, such as mobile computing device, tracking eye movement is becoming increasingly important to be used for various applications and processes, such as user identification, user attention detection, etc. For example, conventional eye tracking techniques are inefficient and ill-equipped to detect all possible degrees of freedom relating to eye tracking and further, such techniques fail to estimate the torsion of the eye(s) of users.

BRIEF DESCRIPTION OF THE DRAWINGS

Embodiments are illustrated by way of example, and not by way of limitation, in the figures of the accompanying drawings in which like reference numerals refer to similar elements.

DETAILED DESCRIPTION

Figure 1:
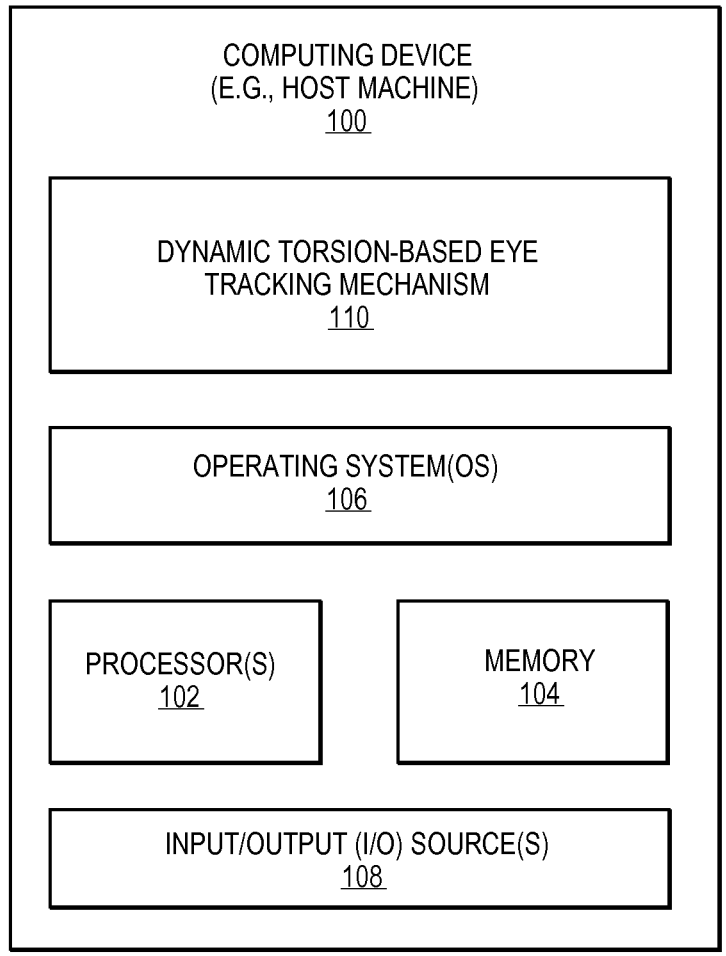
FIG. 1 illustrates a computing device employing a dynamic torsion-based eye tracking mechanism according to one embodiment.

In the following description, numerous specific details are set forth. However, embodiments, as described herein, may be practiced without these specific details. In other instances, well-known circuits, structures and techniques have not been shown in details in order not to obscure the understanding of this description.

Given that human vision is one of the most powerful senses and the human eyes are constantly gazing, their movement can reveal a great deal of information about the human brain, such as what the person is thinking, feeling, watching, expecting, etc. Embodiments provide for an intelligent, efficient, and accurate tracking of eyes by obtaining gaze vectors (such as via torsion motions of the eyes, etc.) using any number of data sensing and capturing devices to better reflect the aforementioned conditions and more that can be deciphered from tracking a human eye. It is contemplated that eye tracking may be referred to as a process of obtaining gaze vectors or gaze points, where a gaze vector refers to a direction of gaze, and where a gaze point refers to a point where that the user views which is usually an intersection of a gaze vector and a screen.

It is contemplated that each gaze vectors correspond to the gaze direction of the eye may then be used for any number of software programs/applications, such as (without limitation): medical devices and/or research, laser refractive surgery, vehicle simulators and/or sensors, sports training, commercial eye tracking (e.g., advertising, Web applications, marketing, automotive, cinema/television, image and/or video compression, user activity recognition, brain response, computer vision, etc.

Embodiments provide for dynamic and efficient estimation of head orientation in relation to an eye tracking camera and further, estimation of the orientation of the camera in the world (e.g., using inertial sensors, etc.) and accordingly, embodiments provide for facilitating estimation of head orientation of users in a world reference frame. This estimation of head orientation may then be used for estimating torsion of the users' eyes.

It is contemplated that a human eye may have three mechanical degrees of freedom, such as left-right orientation (also referred to as "yaw"), up-down orientation (also referred to as "pitch"), and torsional rotation, such as around the eye axil (also referred to as "roll"). In addition consciously managing or controlling two of the three degrees of freedom, such as the left-right orientation, such as yaw, and the up-down orientation, such as pitch. As aforementioned, the third degree of freedom may include torsional rotation, such as around the eye axis, such as roll. This torsional rotation may relate to the following two cases, where the torsional rotation may be (without limitation): 1) spontaneously controlled when an eye gaze point is changed which may follow one or more know laws, such as Donders' law, Listing's laws, etc. (also referred to as "first case" or "second motion"); and 2) compensated for head tilt, where the eye keeps its orientation related to the gravitational horizon of the earth (also referred to as "second case" or "second motion").

Embodiments provide for estimating the aforementioned first and second motions relating to the torsional rotation. It is contemplated that to avoid any inaccuracies, the second motion may be additionally significant when relating to mobile computing devices (e.g., smartphone, tablet computer, etc.) employing mobile eye trackers which may be embedded in such mobile computing devices where a user's head may be tilted up to a particular angle (such as right angle, 90 degrees), such as when a mobile device is used by a user to read in bed, etc.

Figure 2A:
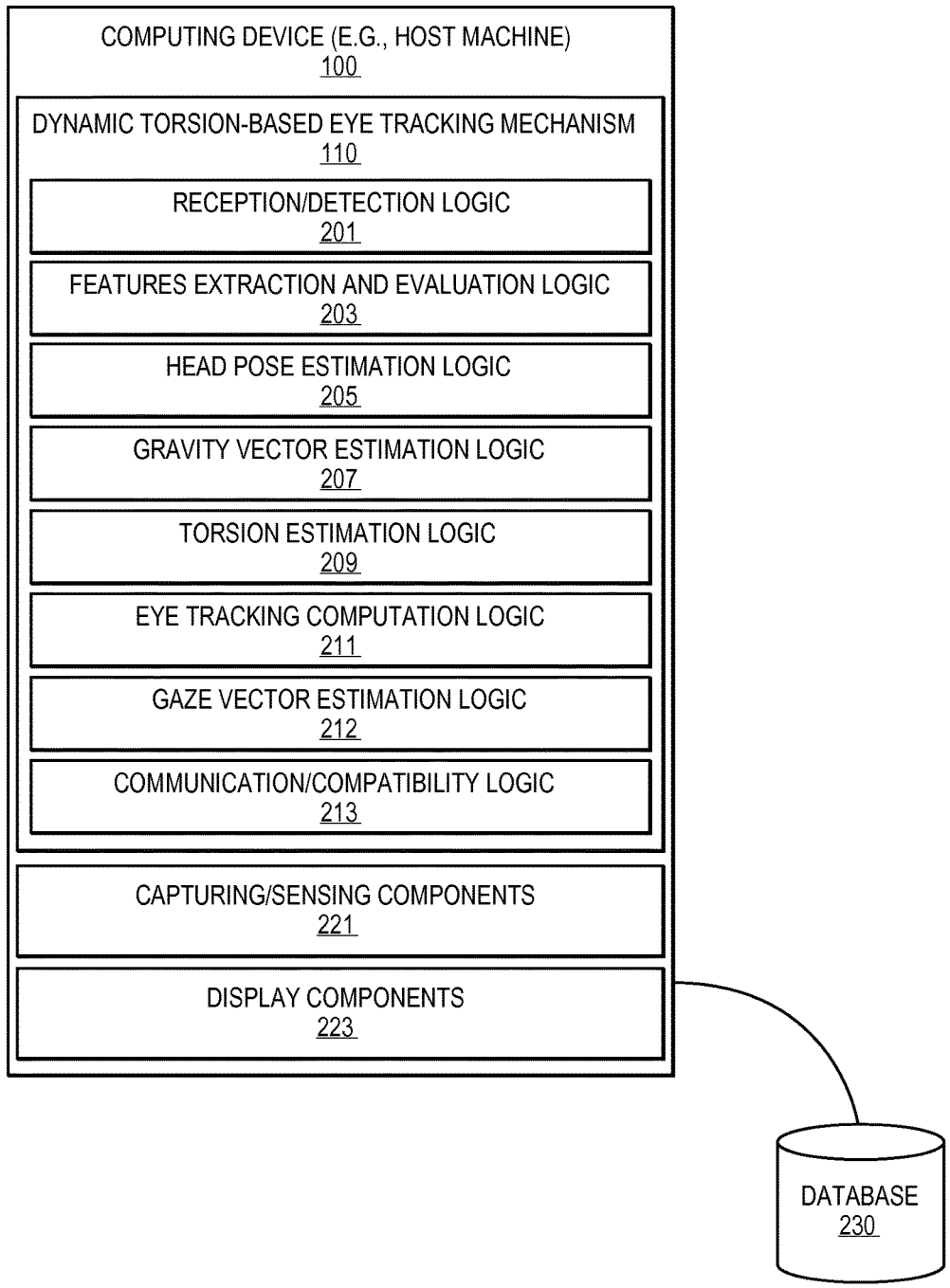
FIG. 2A illustrates a dynamic torsion-based eye tracking mechanism according to one embodiment.

FIG. 1 illustrates a computing device 100 employing a dynamic torsion-based eye tracking mechanism 110 according to one embodiment. Computing device 100 serves as a host machine for hosting dynamic torsion-based eye tracking mechanism ("eye tracking mechanism") 110 that includes any number and type of components, as illustrated in FIG. 2A, to efficiently perform dynamic, intelligent, and efficient estimation of eye torsion for improved and accurate eye tracking as will be further described throughout this document.

Computing device 100 may include any number and type of communication devices, such as large computing systems, such as server computers, desktop computers, etc., and may further include set-top boxes (e.g., Internet-based cable television set-top boxes, etc.), global positioning system ("GPS")-based devices, etc. Computing device 100 may include mobile computing devices serving as communication devices, such as cellular phones including smartphones (e.g., iPhone® by Apple®, BlackBerry® by Research in Motion®, etc.), personal digital assistants ("PDAs"), tablet computers (e.g., iPad® by Apple®, Galaxy 3® by Samsung®, etc.), laptop computers (e.g., notebook, netbook, Ultrabook™ system, etc.), e-readers (e.g., Kindle® by Amazon®, Nook® by Barnes and Nobles®, etc.), media internet devices ("MIDs"), smart televisions, television platforms, intelligent devices, computing dust, media players, wearable devices (e.g., wearable glass (e.g., Google® Glass® by Google®), smartwatch, bracelet, smartcard, jewelry, clothing items, etc.), media players, etc.

Computing device 100 may include an operating system ("OS") 106 serving as an interface between hardware and/or physical resources of the computer device 100 and a user. Computing device 100 further includes one or more processors 102, memory devices 104, network devices, drivers, or the like, as well as input/output ("I/O") sources 108, such as touchscreens, touch panels, touch pads, virtual or regular keyboards, virtual or regular mice, etc.

It is to be noted that terms like "node", "computing node", "server", "server device", "cloud computer", "cloud server", "cloud server computer", "machine", "host machine", "device", "computing device", "computer", "computing system", and the like, may be used interchangeably throughout this document. It is to be further noted that terms like "application", "software application", "program", "software program", "package", "software package", "code", "software code", and the like, may be used interchangeably throughout this document. Also, terms like "job", "input", "request", "message", and the like, may be used interchangeably throughout this document. It is contemplated that the term "user" may refer to an individual or a group of individuals using or having access to computing device 100.

FIG. 2A illustrates a dynamic torsion-based eye tracking mechanism 110 according to one embodiment. In one embodiment, dynamic torsion-based eye tracking mechanism 110 may include any number and type of components, such as (without limitation): detection/reception logic 201; features extraction and evaluation logic 203; head pose estimation logic 205; gravity vector estimation logic 207; torsion estimation logic 209; eye tracking computation logic 211; gaze vector computation logic 213; and communication/compatibility logic 215.

In addition to hosting eye tracking mechanism 110, computing device 100 may further include one or more capturing/sensing devices 221 including one or more capturing devices (e.g., cameras, microphones, sensors, accelerometers, illuminators, etc.) that may be used for capturing any amount and type of data, such as images (e.g., photos, videos, movies, audio/video streams, etc.), audio streams, biometric readings, environmental/weather conditions, maps, etc., where one or more of capturing/sensing device 221, such as a camera, may be in communication with one or more components of eye tracking mechanism 110, such as reception/detection logic 201, to detect and receive images captured by the camera. Such images may then be used for various tasks being performed by eye tracking mechanism 110, such as eye tracking, torsion estimation, etc. It is further contemplated that one or more capturing/sensing devices 221 may further include one or more supporting or supplemental devices for capturing and/or sensing of data, such as illuminators (e.g., infrared ("IR") illuminator of FIG. 2E); light fixtures, generators, sound blockers, etc.

It is further contemplated that in one embodiment, capturing/sensing devices 221 may further include any number and type of sensing devices or sensors (e.g., linear accelerometer) for sensing or detecting any number and type of contexts (e.g., estimating horizon, linear acceleration, etc., relating to a mobile computing device, etc.) which may then be used by eye tracking mechanism 110 to perform one or more tasks relating to torsion estimation and such to for accurate eye tracking as will be further described throughout this document. For example, capturing/sensing devices 221 may include any number and type of sensors, such as (without limitations): accelerometers (e.g., linear accelerometer to measure linear acceleration, etc.); inertial devices (e.g., inertial accelerometers, inertial gyroscopes, micro-electro-mechanical systems ("MEMS") gyroscopes, inertial navigators, etc.); gravity gradiometers to study and measure variations in gravitation acceleration due to gravity, etc. For example, capturing/sensing devices 221 may further include (without limitations): audio/visual devices (e.g., cameras, microphones, speakers, etc.); context-aware sensors (e.g., temperature sensors, facial expression and feature measurement sensors working with one or more cameras of audio/visual devices, environment sensors (such as to sense background colors, lights, etc.), biometric sensors (such as to detect fingerprints, etc.), calendar maintenance and reading device), etc.; global positioning system ("GPS") sensors; resource requestor; and trusted execution environment ("TEE") logic. TEE logic may be employed separately or be part of resource requestor and/or an I/O subsystem, etc.

Computing device 100 may further include one or more display devices 223, such as a display device, a display screen, etc., that may also remain in communication with one or more components of eye tracking mechanism 110, such as communication/compatibility logic 221, to facilitate displaying of images, etc.

Computing device 100 may include a mobile computing device (e.g., smartphone, tablet computer, wearable glasses, such as Google® Glass®, etc.) which may be communication with one or more repositories or database, such as database 230, where any amount and type of data (e.g., torsion estimations, eye tracking data, etc.) may be stored and maintained along with any amount and type of other information and data sources, such as resources, policies, etc., may be stored. Further, computing device 100 may be in communication with any number and type of other computing devices, such as desktop computer, laptop computer, mobile computing device, such as a smartphone, a tablet computer, wearable glasses, etc., over one or more networks, such as cloud network, the Internet, intranet, Internet of Everything ("IoT"), proximity network, Bluetooth, etc.

In the illustrated embodiment, computing device 100 is shown as hosting eye tracking mechanism 110; however, it is contemplated that embodiments are not limited as such and that in another embodiment, eye tracking mechanism 110 may be entirely or partially hosted by multiple devices, such as multiple client computers or a combination of server and client computer, etc. However, throughout this document, for the sake of brevity, clarity, and ease of understanding, eye tracking mechanism 100 is shown as being hosted by computing device 100.

It is contemplated that computing device 100 may include one or more software applications (e.g., website, business application, mobile device application, etc.) in communication with eye tracking mechanism 110, where a software application may offer one or more user interfaces (e.g., web user interface (WUI), graphical user interface (GUI), touchscreen, etc.) to work with and/or facilitate one or more operations or functionalities of eye tracking mechanism 110.

In one embodiment, a camera (e.g., IR camera) of capturing/sensing devices 221 may be used to capture an image of eyes (e.g., human eyes). For example, the image may include both eyes but, in one embodiment, a different gaze vector may be estimated for each eye. The image by the camera may then be communicated to and received or detected by reception/detection 201. Certain features of the image may then be extracted and initially processed by features extraction and evaluation logic 203 where, for example, the pupil contour of the eye along with any reflections of the IR sources (e.g., glints) may be extracted from the image. It is contemplated that gaze vectors (e.g., a separate gaze vector for each eye) may indicate the eyes' gaze points and may be regarded as the main output of the eye tracking process. It is contemplated that an output of a gaze tracker may be gaze points (e.g., points on the screen), gaze vectors, etc.

For example and in one embodiment, features extraction and evaluation logic 203 may be used to extract any amount and type of data relating to various image features of the image of the eye for further processing. This extracted features data may be processed and then used by gaze vector estimation logic 213 to compute or obtain a gaze vectors associated with each eye, where the extracted data may include (without limitation): highly accurate location of glints, pupils, etc.

Figure 2B:
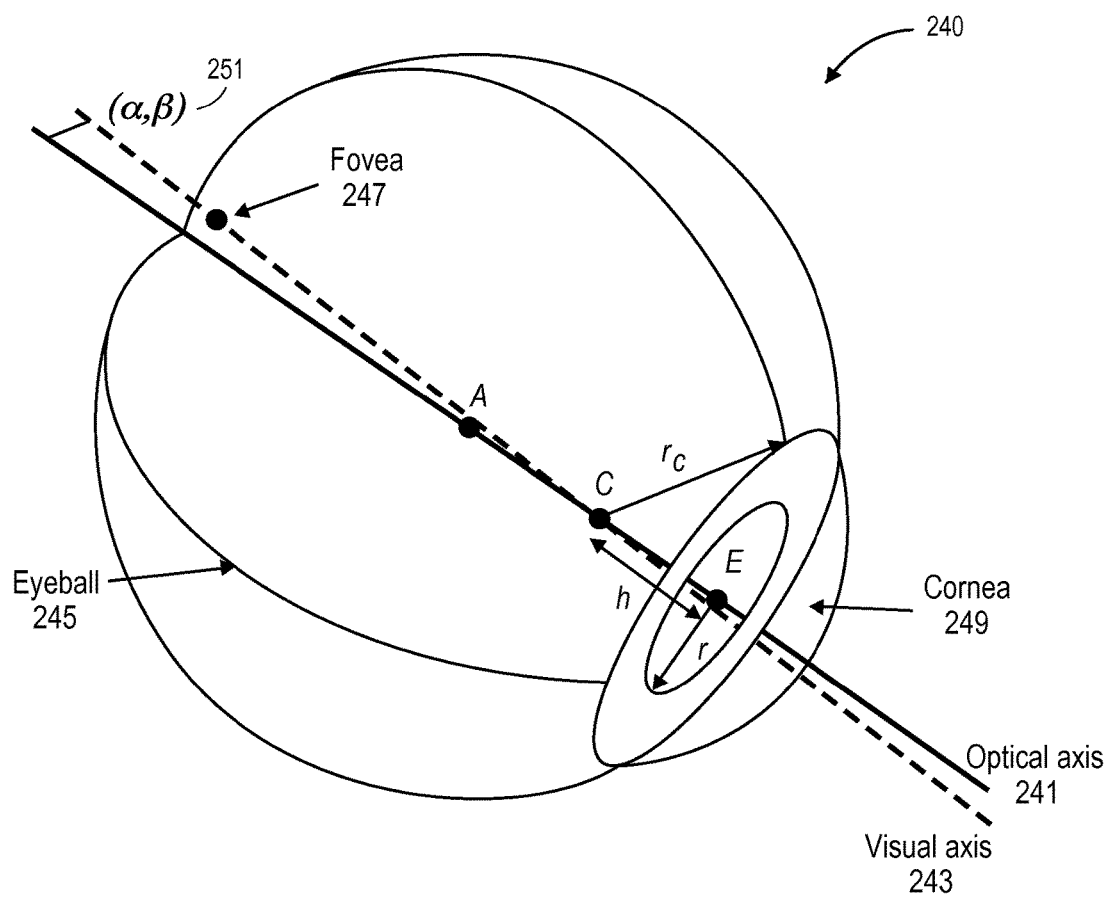
FIG. 2B illustrates an eye according to one embodiment.

In one embodiment, this processing of image features and the eventual estimation of gaze vectors may be achieved by performing one or more of the following tasks (without limitation): 1) estimating, via eye tracking computation logic 211, an optical axis of the eye the image, such as optical axis 241 of eye 240 of FIG. 2B, where the optical axis of the eye refers to a line that passes through the center of curvature of the cornea 249 and runs parallel to the axis of symmetry. It is contemplated that eye 240 may contain cornea 249 and a crystalline lens (which may be used for focus), where reflection may be obtained from cornea 249. Further, a spherical mirror may be regarded as a mathematical model of cornea 249, and not a physical feature of eye 240. As will be further described below, using eye tracking computation logic 211, any parameters of the optical axis may be computed based on one or more of the image features, the radius of curvature of the cornea, and the distance of the cornea center of curvature and the pupil plane as extracted by features extraction and evaluation logic 203; and 2) estimating, via gaze vector estimation logic 213, a visual axis of the eye in the image, such as visual axis 243 of eye 240 FIG. 2B, where the visual axis of the eye refers to a line that passes through the center of vision, such as through fovea 247 of FIG. 2B, and the (optical) nodal point of the eye.

Further, as illustrated in FIG. 2B, visual axis 243 may divert from optical axis 241 by an angle which is known as kappa ("κ") 251, where κ may include two components, such as a horizontal angle α (alpha) and a lateral angle β (beta). For example, an average values for a may be 5° and for β may be 1.5°. It is contemplated that angle κ may be different for each person, such as from person to person, as well as being different for each eye, such as the left and the right eye. Further, κ may be measured for each individual by a calibration process.

Figure 2C:
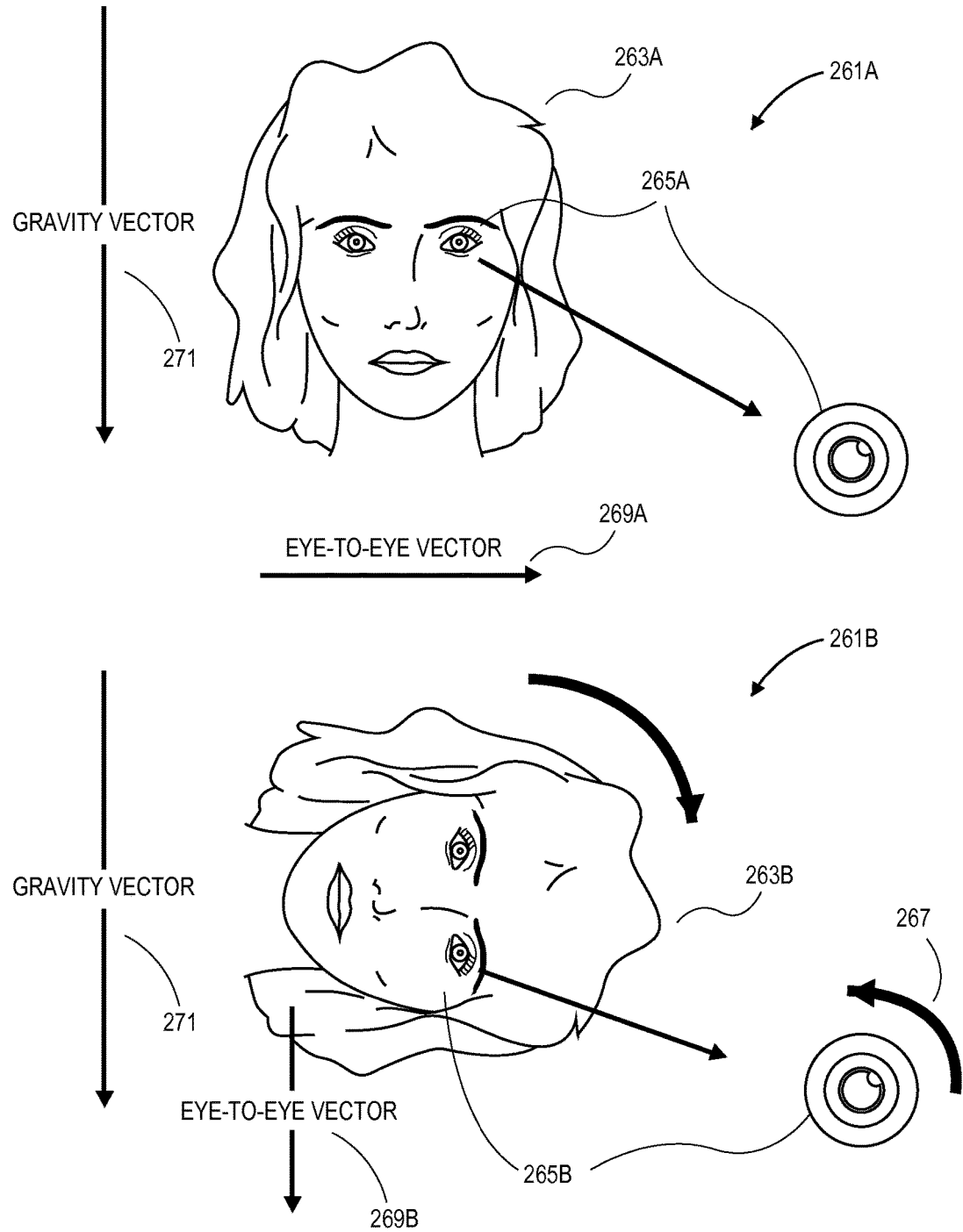
FIG. 2C illustrates images that are captured and processed according to one embodiment.

In one embodiment, the visual axis may be obtained based on the optical axis by computing κ and the three-axes pose of the eye. Similarly, the pitch and yaw angles of the eye may also be obtained or known from the optical axis, while the roll angle may be obtained from one or more empirical laws, such as (without limitation) Donders' law (which states that the orientation of the eye when looking in a specific direction is always the same), Listing's law (which states that the axis of rotation of the eye lies in a common plane ("torsion free") and the plane is perpendicular to the optical axis), etc. In some embodiments, the aforementioned laws may be valid in one or more conditions, such as the laws are valid when the head is erect (in relation of the gravity). For example, when the head is tilted (such head 263A of image 261A being tilted into tilted head 263B of image 261B as illustrated in FIG. 2C), the eyes may perform a torsion motion in order to compensate for the rotation (such as torsion-free eye 265A of head 263A performs a torsion motion 267 when it is turned into tilted eye 265B of tilted head 265B as illustrated in FIG. 2C). Accordingly, in some embodiments, obtaining or knowing the head tilt may be useful in accurately estimating the visual axis which may then be used to accurately estimate a torsion angle, ψ, such as torsion angle 273 of FIG. 2D.

In one embodiment, upon extraction and evaluation of the image features by features extraction and evaluation logic 203, head pose estimation logic 205 may be triggered to perform estimation of the head pose based on the eye position of the eyes as obtained from the image by extraction and evaluation logic 203, where the image may be captured by one or more of capturing/sensing devices 221 (e.g., an IR camera, etc.) of FIG. 2A. In one embodiment, a full three-dimensional ("3D") pose of the head (such as including one or more of the three mechanical degrees of freedom (e.g., roll, pitch, and yaw)) may be achieved by using one or more image-based head pose estimation techniques as facilitated by head pose estimation logic 205. In another embodiment, an eye tracker may be mounted on a smart device, such as on a wearable glass (e.g., Google® Glass®, etc.), such that the head pose may be estimated directly from a gravity vector and a fixed rotation due to the alignment of the smart device on the user head. Further, in one embodiment, a 3D position of both eyes in the image may be used to estimate the head tilt of the head of the person in the image using one or more 3D-based estimation techniques to further improve the image-based pose estimation as facilitated by head pose estimation logic 205.

In one embodiment, once the head pose has been estimated, gravity vector estimation logic 207 may be triggered to perform gravity vector estimation. For example, gravity vector estimation may be performed based on sensor-obtained data (e.g., accelerometer data) obtained by and received from one or more capturing/sensing devices 221 (e.g., linear accelerometer) of FIG. 2A using one or more gravity vector estimation techniques as facilitated by gravity vector estimation logic 207.

In one embodiment, torsion estimation logic 209 may be used to perform torsion estimation processes to obtain a final torsion value. For example and in one embodiment, estimation for Listing's torsion angle, $\psi_{Listing}$, may be performed based on data relating to the head pose as estimated by and received from head pose estimation logic 205. Similarly, using torsion estimation logic 209, estimation for tilt torsion angle, $\psi_{tilt}$, may be performed using data relating to gravity vector as obtained by gravity vector estimation logic 207. In one embodiment, the torsion angle may be computed as the angle between the left-eye-to-right-eye-vector and the gravity vector in a vertical plane as, illustrated in FIGS. 2C-2D, where the vertical plane may refer to the plane that contains the gravity vector and the eye.

Further, in one embodiment, in applying Donders' and Listing's laws, the Listing's torsion angle may be derived by torsion estimation logic 209 using the following equation:

$$\sin\psi_{Listing} = \frac{\sin\theta \cdot \sin\phi}{1 + \cos\theta \cdot \cos\phi},$$

where $\theta$, $\phi$ represent the horizontal rotation angle and vertical rotation angle, respectively, of the optical axis relative to the eye's rest position. Further, $\theta$, $\phi$ may be computed and regarded as an angular difference of the head frontal direction and the eye's optical axis. In one embodiment, the final/total torsion angle, $\psi$, may be obtained by adding the tilt torsion angle to the Listing's torsion angle, as predicted by the Donders' and Listing's laws, such as: total torsion $\psi = \psi_{tilt} + \psi_{Listing}$.

In one embodiment, using eye tracking computation logic 211 and as discussed with reference to FIGS. 2A-2B, an optical axis may be estimated for each eye and the estimated optical axis may then be used as an input for one or more processes, such as torsion estimations, gaze vector estimation, etc.

Moreover, in one embodiment and as discussed with reference to FIGS. 2A-2B, a visual axis may be computed based on the optical axis using the newly-estimated torsion parameters as obtained from the aforementioned torsion estimations and one or more image orientations, such as yaw and pitch. In one embodiment, using gaze vector estimation logic 212, the visual axis may be estimated as follows: VisualAxis=$R_{OpticalAxis} \cdot R_{Torsion} \cdot R_{Calibration} \cdot$OpticalAxis$_0$, where OpticalAxis$_0$ refers to the optical axis of the eye at its resting position (e.g., looking forward), where $R_{Calibration}$ refers to a transformation (e.g., rotation around the eyes nodal point) that rotates by ($\alpha$, $\beta$), and where $R_{Torsion}$ and $R_{OpticalAxis}$ refer to transformations of the optical axis, as estimated by the eye tracker (e.g., yaw, pitch). Further, the rest optical axis may be rotated by ($\alpha$, $\beta$) and then by the total torsion angle, $\psi$, and then further by the pitch and yaw orientations.

As aforementioned, OpticalAxis$_0$ may be derived based on the head pose estimation and the eye position of each of the eyes in the image. Further, $R_{Calibration}$ may refer to the result of ($\alpha$, $\beta$) which, stated different, may be the result of torsion estimation and measured a priori using the following equation $$R_{Torsion} = \begin{bmatrix} \cos(\psi) & -\sin(\psi) & 0 \\ \sin(\psi) & \cos(\psi) & 0 \\ 0 & 0 & 1 \end{bmatrix},$$

when applied to an eye coordinate system.

Similarly, in one embodiment, $R_{OpticalAxis}$ may refer to the result of the eye tracking computation, as facilitated by eye tracking computation logic 211, such as:

$$OpticalAxis = \begin{bmatrix} \sin(\theta) \cdot \cos(\phi) \\ \sin(\phi) \\ -\cos(\theta) \cdot \cos(\phi) \end{bmatrix},$$

where $\theta$ refers to the horizontal rotation and where $\phi$ refers to vertical rotation angles. Therefore, $$R_{OpticalAxis} = \begin{bmatrix} \cos(\theta) & 0 & -\sin(\theta) \\ 0 & 1 & 0 \\ \sin(\theta) & 0 & \cos(\theta) \end{bmatrix} \cdot \begin{bmatrix} 1 & 0 & 0 \\ 0 & \cos(\phi) & -\sin(\phi) \\ 0 & \sin(\phi) & \cos(\phi) \end{bmatrix}.$$

For example and in one embodiment, a coordinate system may be used, where x refers to the horizontal direction, y refers to the vertical direction, and z is the forward direction and thus, $$OpticalAxis = \begin{bmatrix} 0 \\ 0 \\ 1 \end{bmatrix},$$

assuming $\alpha = 5°$, $\beta = 0$, which implies $$R_{Calibration} = \begin{bmatrix} \cos(5°) & 0 & \sin(5°) \\ 0 & 1 & 0 \\ -\sin(5°) & 0 & \cos(5°) \end{bmatrix},$$

and assuming a head tilt of 90°, which implies $$R_{Torsion} = \begin{bmatrix} \cos(90°) & \sin(90°) & 0 \\ -\sin(90°) & \cos(90°) & 0 \\ 0 & 0 & 1 \end{bmatrix},$$

and optical axis direction forwards (0 pitch, 0 yaw), which implies $$R_{OpticalAxis} = \begin{bmatrix} 1 & 0 & 0 \\ 0 & 1 & 0 \\ 0 & 0 & 1 \end{bmatrix}.$$

Accordingly, the result may be $$VisualAxis = \begin{bmatrix} \sin(5°) \\ 0 \\ \cos(5°) \end{bmatrix} = \begin{bmatrix} 0.0872 \\ 0 \\ 0.9962 \end{bmatrix},$$

where, for example, ignoring the head tilt, $$R_{Torsion} = \begin{bmatrix} 1 & 0 & 0 \\ 0 & 1 & 0 \\ 0 & 0 & 1 \end{bmatrix},$$

which may result in a 5° bias, where one or more eye tracking applications (e.g., commercial eye tracking applications) may necessitate an accuracy of <1°.

Figure 3:
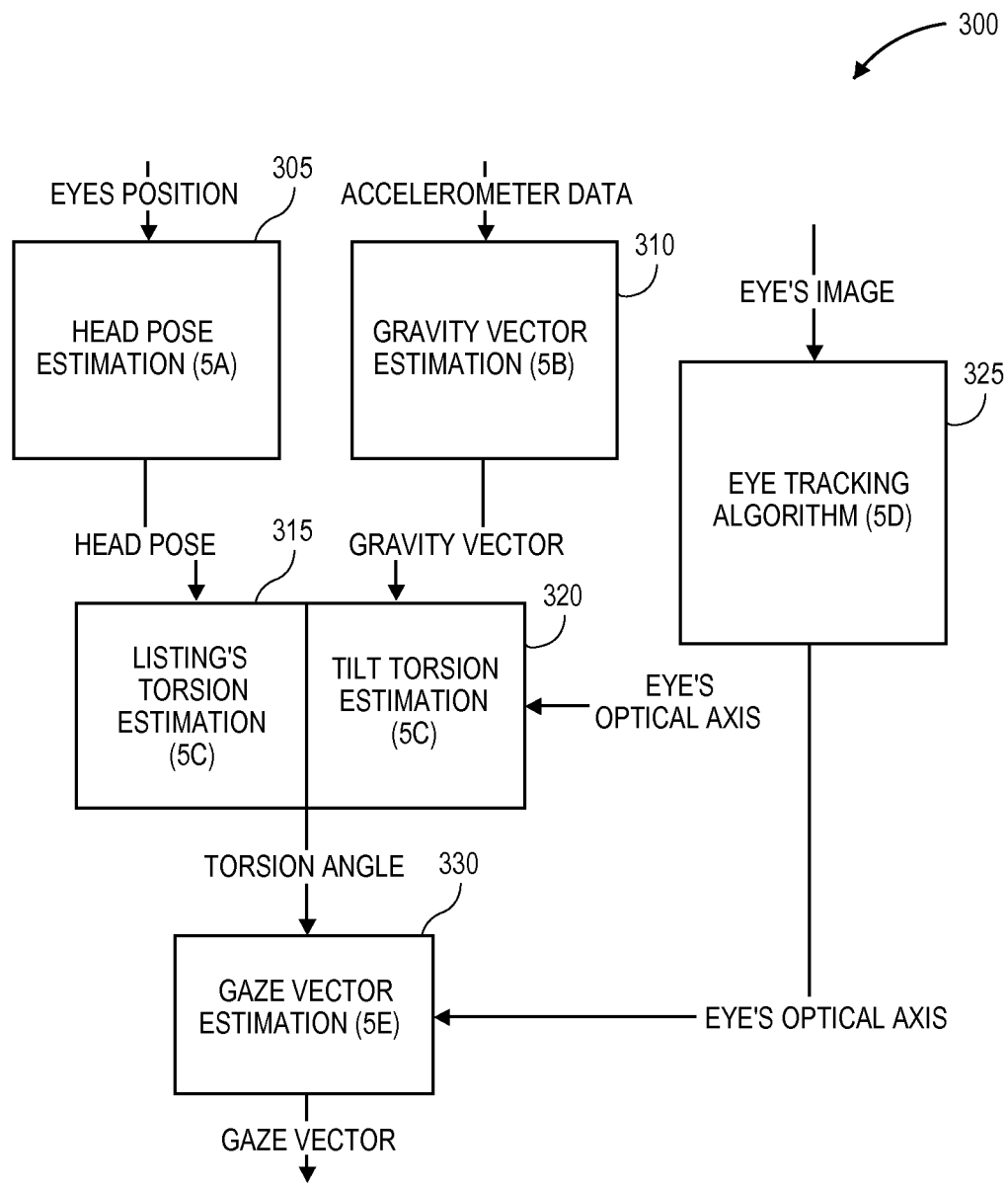
FIG. 3 illustrates a method for facilitating eye torsion-based accurate tracking of eyes according to one embodiment according to one embodiment.

In one embodiment, as illustrated with respect to FIG. 3, the total torsion angle and one or more axes relating to the eye (e.g., optical axis, visual axis, etc.) and any other relevant information may be used to estimate gaze vector for each eye as facilitated by gaze vector estimation logic 330. It is contemplated that each gaze vector may correspond to an eye and can be used to determine gazing patterns for that eye. Such gazing patterns may be used for accurate tracking of eyes which may then be used for any number of applications, such as (without limitation): medical devices and/or research, laser refractive surgery, vehicle simulators and/or sensors, sports training, commercial eye tracking (e.g., advertising, Web applications, marketing, automotive, cinema/television, image and/or video compression, user activity recognition, brain response, computer vision, etc.

In one embodiment, images may be captured capturing/sensing devices 221, processed via eye tracking mechanism 110, and displayed via display devices 223. It is contemplated that eye tracking mechanism 110 may be used with and in communication with one or more software applications, such as one or more email applications (e.g., Gmail®, Outlook®, company-based email, etc.), text or phone using one or more telecommunication applications (e.g., Skype®, Tango®, Viber®, default text application, etc.), social/business networking websites (e.g., Facebook®, Twitter®, LinkedIn®, etc.), or the like.

Communication/compatibility logic 213 may be used to facilitate dynamic communication and compatibility between computing device 100 and any number and type of other computing devices (such as mobile computing device, desktop computer, server computing device, etc.), processing devices (such as central processing unit (CPU), graphics processing unit (GPU), etc.), capturing/sensing devices 213 (e.g., data capturing and/or sensing instruments, such as camera, sensor, illuminator, etc.), display devices 223 (such as a display device, display screen, display instruments, etc.), user/context-awareness components and/or identification/verification sensors/devices (such as biometric sensor/detector, scanner, etc.), memory or storage devices, databases and/or data sources (such as data storage device, hard drive, solid-state drive, hard disk, memory card or device, memory circuit, etc.), networks (e.g., cloud network, the Internet, intranet, cellular network, proximity networks, such as Bluetooth, Bluetooth low energy (BLE), Bluetooth Smart, Wi-Fi proximity, Radio Frequency Identification (RFID), Near Field Communication (NFC), Body Area Network (BAN), etc.), wireless or wired communications and relevant protocols (e.g., Wi-Fi®, WiMAX, Ethernet, etc.), connectivity and location management techniques, software applications/websites, (e.g., social and/or business networking websites, such as Facebook®, LinkedIn®, Google+®, Twitter®, etc., business applications, games and other entertainment applications, etc.), programming languages, etc., while ensuring compatibility with changing technologies, parameters, protocols, standards, etc.

Throughout this document, terms like "logic", "component", "module", "framework", "engine", "point", "tool", and the like, may be referenced interchangeably and include, by way of example, software, hardware, and/or any combination of software and hardware, such as firmware. Further, any use of a particular brand, word, term, phrase, name, and/or acronym, such as "image", "cut", "vision technique", "gesture", "hand-forearm", "ratio", "threshold", "axis", "vertical", "horizontal", "iteration", "calculation", "extreme points", "hysteresis points", "hypothesis cuts", "text" or "textual", "photo" or "image", "video", "social networking website", "logic", "engine", "module", etc., should not be read to limit embodiments to software or devices that carry that label in products or in literature external to this document.

It is contemplated that any number and type of components may be added to and/or removed from eye tracking mechanism 110 to facilitate various embodiments including adding, removing, and/or enhancing certain features. For brevity, clarity, and ease of understanding of eye tracking mechanism 110, many of the standard and/or known components, such as those of a computing device, are not shown or discussed here. It is contemplated that embodiments, as described herein, are not limited to any particular technology, topology, system, architecture, and/or standard and are dynamic enough to adopt and adapt to any future changes.

Referring now to FIG. 2B, it illustrated an eye 240 according to one embodiment. In the illustrated embodiment, proper locations of eyeball 245 and cornea 249 are provided which may then be used to determine fovea 247 and optical axis 241 which may then be used to compute visual axis 243 and kappa angle 251 as will be further discussed with reference to the subsequent figures.

FIG. 2C illustrates images 261A, 261B that are captured and processed according to one embodiment. In the illustrated embodiment, image 261A shows an image of a person's face having two eyes of which eye 265A is to be tracked. Image 261A further illustrates and includes head 263A that is shown to be straight and vertical with respect to the earth, where the earth is the source of gravitational force (or simply referred to as "gravity"). Accordingly, as illustrated, gravity vector 271 is shown as pointing downwards and eye-to-eye vector 269A is shown to be sideways or horizontal with respect to the earth and perpendicular with respect to gravity vector 271.

As illustrated in a subsequent image, such as image 261B, the upward and straight head 263A of image 261A is shown to be tilted as head 263B which is now perpendicular or 90° with respect to head 263A. It is contemplated and as illustrated, head 263B also tilts eye-to-eye vector 269A to now eye-to-eye vector 269B which is now parallel to gravity vector 271. This tilt also shift the position of the eyes, such as eye 265A being tilted along with head 263B is now shown to be at a new position as eye 265B which causes it to perform torsion motion 267.

Figure 2D:
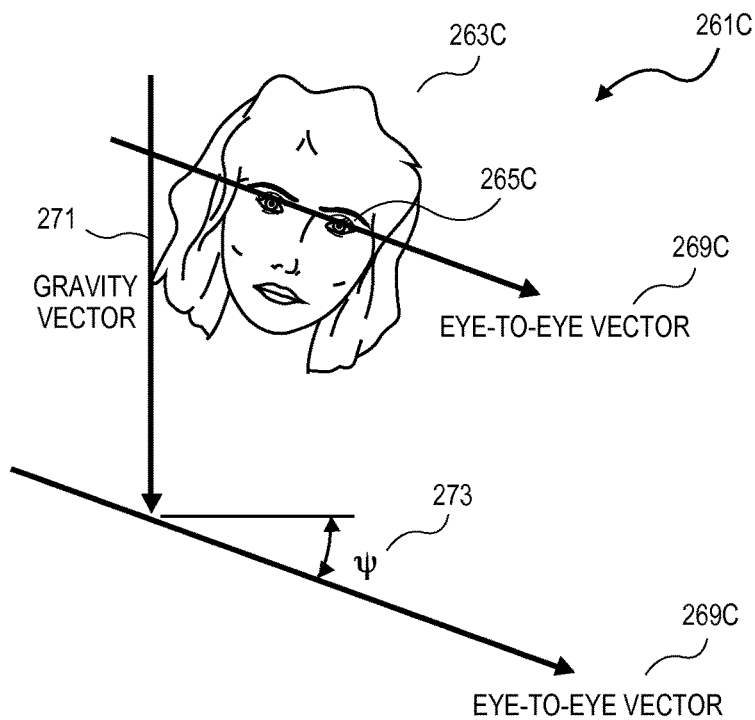
FIG. 2D illustrates an image that is captured and processed according to one embodiment.

FIG. 2D illustrates image 261C that is captured and processed according to one embodiment. As illustrated, image 261C may be a continuation of images 261A, 261B of FIG. 2C where now head 263C is shown to be tilted away at a smaller angle from head 263A when compared to tilting angle of head 263B and/or with respect to the earth and gravity vector 271. In the illustrated embodiment, with this tilted head 263C, eye 265C is now in a new tilted position as is eye-to-eye vector 269C with respect to, for example, gravity vector 271. In one embodiment and as illustrated, this tilt of the head, such as from head 263A to head 263C and the corresponding tilt from eye 265A and eye 265C causing torsion motion 267, produces an angle between the initial eye-to-eye vector 269A and the new eye-to-eye vector 269C which respect to the constant gravity vector 271. This angle, being caused by torsion motion 267, is to be estimated as torsion angle 273.

Figure 2E:
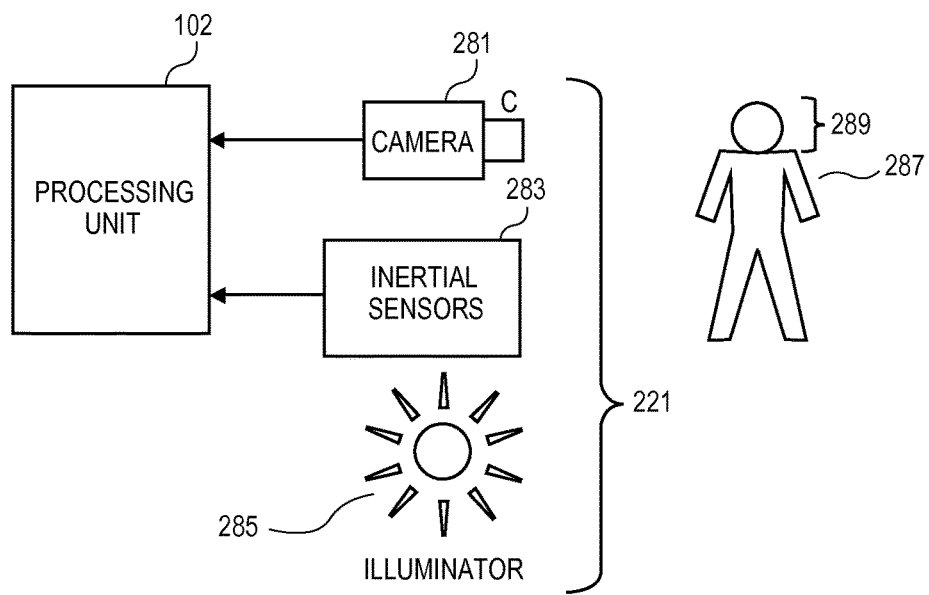
FIG. 2E illustrates one or more capturing and sensing devices to be used for efficient estimation of eye torsion for improved and accurate tracking of eye according to one embodiment.

FIG. 2E illustrates one or more capturing and sensing devices 281-285 to be used for eye torsion-based accurate tracking of eyes according to one embodiment. As aforementioned, any number and type of components (e.g., cameras, sensors, display devices, etc.) may be used along with eye tracking mechanism 110 of FIG. 2A to perform one or more tasks relating to estimation of eye torsion and tracking of eye. For example, the illustrated embodiment displays a set 281-285 of capturing/sensing devices 221 being used for image capturing, such as capturing one or more images of face 289 of person 287. It is contemplate that any image of face 289 may also include an image of the eyes of person 287 which may then be used to determine poses and tilts of the head corresponding to face 289 to be used for various estimations and calculations as described throughout this document. It is contemplated that the image may be part of or obtained from a video stream or a still picture, or the like.

In one embodiment, the illustrated components 281-285 of capturing/sensing devices 221 include one or more cameras 281 (e.g., IR camera, etc.) to be used, for example, along or in communication with one or more inertial sensors 283 (e.g., inertial accelerometer, linear accelerometer, etc.) and one or more illuminators 285 (e.g., IR illuminator, etc.) to provide the necessary and/or desired illumination. Further, as illustrated, these components 281-285 may be used in communication with one or more processing units, such as processor(s) 102 of FIG. 1, to facilitate the various tasks of eye tracking mechanism 110 of FIG. 2A. For example and in one embodiment, a combination of inertial sensors 283 and the head pose of person 287 as captured by camera 281 using illuminator 285 may be used to obtain and/or estimate the relevant values to determine the eye torsion for eye tracking as described with reference to FIG. 3 as well as throughout this document.

FIG. 3 illustrates a method 300 for facilitating eye torsion-based accurate tracking of eyes according to one embodiment according to one embodiment. Method 300 may be performed by processing logic that may comprise hardware (e.g., circuitry, dedicated logic, programmable logic, etc.), software (such as instructions run on a processing device), or a combination thereof. In one embodiment, method 300 may be performed by eye tracking mechanism 110 of FIG. 1. The processes of method 300 are illustrated in linear sequences for brevity and clarity in presentation; however, it is contemplated that any number of them can be performed in parallel, asynchronously, or in different orders. For brevity, many of the details discussed with reference to FIGS. 1 and 2A-E may not be discussed or repeated hereafter.

As aforementioned, embodiments provide for an eye tracking system that is based on using various capturing/sensing devices 221 of FIG. 2A, such as IR cameras, IR illuminators, linear accelerometers, etc., where, for example, and IR camera may capture the image of an eye. The image may then be processed, such as the contour relating to the eye may be extracted as well as the reflection (e.g., glints) from any IR sources (e.g., IR light source, etc.). In one embodiment, gaze vectors relating to the eyes may be accurately estimated and regarded as the main output for eye tracking such that these gaze vectors may be used for intelligent and accurate eye tracking. It is contemplated gaze vectors indicate gaze patterns and may be different for each eye as well as for each individual, and the like, and used for various purposes and software programs.

Method 300 beings at block 305 with estimation of head poses (e.g., head tilts) of the image using 3D positions of the eyes of the person in the image as shown in FIGS. 2C-2D. For example and in one embodiment, a full 3D pose of the head, which may include one or more of a roll, a pitch, and a yaw, may be achieved by using one or more image-based head pose estimation techniques as facilitated by head pose estimation logic 205 of FIG. 2A. Further, a 3D position of both eyes of the image may be used to estimate the head tilt of the head of the person in the image using one or more 3D-based estimation techniques to further improve the image-based pose estimation. Further, with regard to head pose estimation's process, at block 305, for incorporation of 3D positions of the eyes with image-based pose estimation, the 3D positions of eyes may help determine the roll and yaw degree of freedom which the pitch remain undetermined. For example, in one embodiment, two estimators may be used to 1) estimate (or assume) the noise of the roll, yaw as estimated from the 3D positions of the eyes, and the noise as estimated by the image-based pose estimation; and 2) compute a maximum likelihood mixture of the two measurement (e.g., from 3D eyes measurement, and image-based measurement).

At block 310, gravity vector estimation logic 207 of FIG. 2A is triggered to perform gravity vector estimation based on the detected/sensed data (e.g., accelerometer data, etc.) received from one or more of capturing/sensing devices 221 (e.g., linear accelerometer, etc.) of FIG. 2A and using one or more gravity vector estimation techniques. In one embodiment, at block 315, Listing's torsion is estimated by torsion estimation logic 209 of FIG. 2A using the head pose data obtained from the aforementioned head pose estimation of block 305. As further discussed with reference to FIG. 2A, applying Donders' and Listing's laws, Listing's torsion angle, $\psi_{Listing}$, is derived using the following equation:

$$\sin\psi_{Listing} = \frac{\sin\theta \cdot \sin\phi}{1 + \cos\theta \cdot \cos\phi},$$

where $\theta$, $\phi$ represent the horizontal rotation angle and vertical rotation angle, respectively, of the optical axis relative to the eye's rest position.

Similarly, at block 320, torsion estimation logic 209 of FIG. 2A facilitates tilt torsion estimation based on the gravity vector data obtained from the aforementioned gravity vector estimation of block 310. As further discussed with reference to FIG. 2A, a tilt-related torsion angle, $\psi_{tilt}$, may be computed as the angle between the left-eye-to-right-eye-vector and the gravity vector in a vertical plane as, illustrated in FIGS. 2C-2D, where the vertical plane may refer to the plane that contains the gravity vector and the eye. Using the tilt and Listing's torsion angles, a total torsion angle may be obtained, such as by simply adding the tilt torsion angle to the Listing's torsion angle as predicted by the Donders' and Listing's laws, such as: total torsion $\psi = \psi_{tilt} + \psi_{Listing}$.

Further, regarding head tilting-related torsion computation, at block 320, using information obtained from accelerometers (e.g., accelerometer data, etc.), a linear accelerometer may be used to produce measurements of the acceleration in various axes/coordinates, such as x, y, z axes AX, AY, AZ (in own coordinate system). Moreover, assuming that the acceleration at the moment is gravitational acceleration, then the gravitational acceleration may be AX, AY, AZ. If detected that the system may not be affected by additional acceleration by looking at the magnitude of the acceleration vector, such as $\sqrt{(AX^2 + AY^2 + AZ^2}$, if this magnitude may not be significantly different from the known acceleration gravity (~9.8 meter/sec^2), we may assume that the only acceleration may be gravitational acceleration.

In one embodiment, at block 325, using the image of the eyes, an optical axis may be estimated for each eye as facilitated by eye tracking computation logic 211 of FIG. 2A and as further illustrated with reference to FIGS. 2A-2B. This estimated optical axis may then be used as an input for one or more of torsion estimation at block 320 and gaze vector estimation at block 330, etc. In further explaining the process at block 325, a couple of corneal reflections (e.g., glints) may be found and using optical geometry and a pre-knowledge of the system (e.g., lights, camera, etc.) geometry and a cornea-radius of curvature may compute a cornea center of curvature. Then, a pupil contour may be found and using optical geometry and the (a-priori known) distance between a pupil plane and the cornea center of curvature, a 3D pupil center may be computed. The vector between the 3D cornea center of curvature and the 3D pupil center may be regarded as the optical axis. Further, the visual axis is generated by the gaze estimation process, at block 330, based on the optical axis and performing a calibration transformation.

At block 330, in one embodiment, as discussed with reference to FIGS. 2A-2B, gaze vector estimation logic 212 may be used to estimate a visual axis for each eye based on the corresponding optical axis and using the new torsion parameters or angles, as obtained in blocks 315, 320, as well as the yaw and pitch orientations of the image. The visual axis may be estimates as follows: VisualAxis=$R_{OpticalAxis} \cdot R_{Torsion} \cdot R_{Calibration} \cdot$OpticalAxis$_0$, where OpticalAxis$_0$ refers to the optical axis of the eye at its resting position (e.g., looking forward), and where $R_{Calibration}$ refers to a transformation (e.g., rotation around the eyes nodal point) that rotates by $(\alpha,\beta)$, and where $R_{Torsion}$ and $R_{OpticalAxis}$ refer to a transformation of the optical axis, as estimated by the eye tracker (e.g., yaw, pitch). Further, the rest optical axis may be rotated by $(\alpha,\beta)$ and then by the total torsion angle, $\psi$, and then further by the pitch and yaw. Similarly, in one embodiment, OpticalAxis$_0$ may be obtained from the head pose estimation using the positions of the eyes in the image as discussed with reference to block 305.

Further, in one embodiment, having estimated the visual axis for each eye as described above, the visual axis along with the eye's optical axis and the total torsion angle may then be used by gaze vector estimation logic 212 of FIG. 2A to estimate gaze vector for each eye. It is contemplated that each gaze vector may correspond to an eye and can be used to determine gazing patterns for that eye, where such gazing patterns may be used for accurate tracking of eyes which may then be used for any number of commercial and non-commercial software programs or applications. It is contemplated that an accurate eye tracking may facilitate a better and more accurate performance from any software application employing the eye tracking.

Further, with regard to gaze vector estimation of block 330, eye tracking may be synonymously referred to as gaze tracking, where gaze vector and gaze point (such as an intersection of gaze vector and the screen) are essentially a final output of the eye tracking process, such as using eye tracking algorithm of block 325. The transformation of the optical axis to the visual axis, as described with reference to block 330, such as:

$$\text{VisualAxis}=R_{OpticalAxis} \cdot R_{Torsion} \cdot R_{Calibration} \cdot \text{OpticalAxis}_0$$

The optical axis (without calibration) may appear as: OpticalAxis=$R_{OpticalAxis} \cdot$OpticalAxis$_0$, where the visual axis, if the tilt-related torsion is ignored, may be as follows:
VisualAxis=$R_{OpticalAxis} \cdot R_{Listing's\ Torsion} \cdot$
$R_{Calibration} \cdot$OpticalAxis$_0$, as aforementioned.

Figure 4:
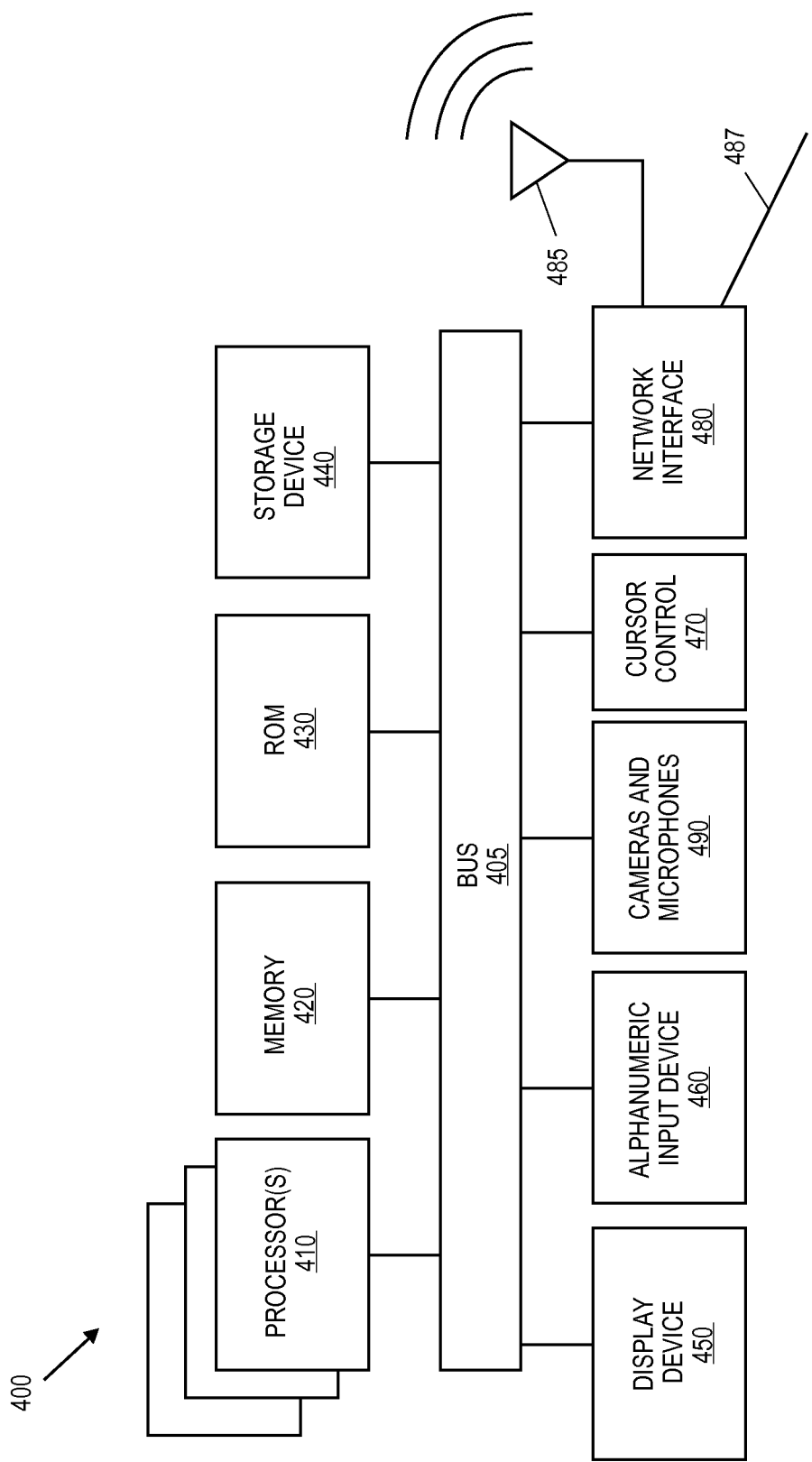
FIG. 4 illustrates computer system suitable for implementing embodiments of the present disclosure according to one embodiment.

FIG. 4 illustrates an embodiment of a computing system 400. Computing system 400 represents a range of computing and electronic devices (wired or wireless) including, for example, desktop computing systems, laptop computing systems, cellular telephones, personal digital assistants (PDAs) including cellular-enabled PDAs, set top boxes, smartphones, tablets, wearable devices, etc. Alternate computing systems may include more, fewer and/or different components. Computing device 400 may be the same as or similar to or include computing devices 100 described in reference to FIG. 1.

Computing system 400 includes bus 405 (or, for example, a link, an interconnect, or another type of communication device or interface to communicate information) and processor 410 coupled to bus 405 that may process information. While computing system 400 is illustrated with a single processor, it may include multiple processors and/or co-processors, such as one or more of central processors, image signal processors, graphics processors, and vision processors, etc. Computing system 400 may further include random access memory (RAM) or other dynamic storage device 420 (referred to as main memory), coupled to bus 405 and may store information and instructions that may be executed by processor 410. Main memory 420 may also be used to store temporary variables or other intermediate information during execution of instructions by processor 410.

Computing system 400 may also include read only memory (ROM) and/or other storage device 430 coupled to bus 405 that may store static information and instructions for processor 410. Date storage device 440 may be coupled to bus 405 to store information and instructions. Date storage device 440, such as magnetic disk or optical disc and corresponding drive may be coupled to computing system 400.

Computing system 400 may also be coupled via bus 405 to display device 450, such as a cathode ray tube (CRT), liquid crystal display (LCD) or Organic Light Emitting Diode (OLED) array, to display information to a user. User input device 460, including alphanumeric and other keys, may be coupled to bus 405 to communicate information and command selections to processor 410. Another type of user input device 460 is cursor control 470, such as a mouse, a trackball, a touchscreen, a touchpad, or cursor direction keys to communicate direction information and command selections to processor 410 and to control cursor movement on display 450. Camera and microphone arrays 490 of computer system 400 may be coupled to bus 405 to observe gestures, record audio and video and to receive and transmit visual and audio commands.

Computing system 400 may further include network interface(s) 480 to provide access to a network, such as a local area network (LAN), a wide area network (WAN), a metropolitan area network (MAN), a personal area network (PAN), Bluetooth, a cloud network, a mobile network (e.g., 3$^{rd}$ Generation (3G), etc.), an intranet, the Internet, etc. Network interface(s) 480 may include, for example, a wireless network interface having antenna 485, which may represent one or more antenna(e). Network interface(s) 480 may also include, for example, a wired network interface to communicate with remote devices via network cable 487, which may be, for example, an Ethernet cable, a coaxial cable, a fiber optic cable, a serial cable, or a parallel cable.

Network interface(s) 480 may provide access to a LAN, for example, by conforming to IEEE 802.11b and/or IEEE 802.11g standards, and/or the wireless network interface may provide access to a personal area network, for example, by conforming to Bluetooth standards. Other wireless network interfaces and/or protocols, including previous and subsequent versions of the standards, may also be supported.

In addition to, or instead of, communication via the wireless LAN standards, network interface(s) 480 may provide wireless communication using, for example, Time Division, Multiple Access (TDMA) protocols, Global Systems for Mobile Communications (GSM) protocols, Code Division, Multiple Access (CDMA) protocols, and/or any other type of wireless communications protocols.

Network interface(s) 480 may include one or more communication interfaces, such as a modem, a network interface card, or other well-known interface devices, such as those used for coupling to the Ethernet, token ring, or other types of physical wired or wireless attachments for purposes of providing a communication link to support a LAN or a WAN, for example. In this manner, the computer system may also be coupled to a number of peripheral devices, clients, control surfaces, consoles, or servers via a conventional network infrastructure, including an Intranet or the Internet, for example.

It is to be appreciated that a lesser or more equipped system than the example described above may be preferred for certain implementations. Therefore, the configuration of computing system 400 may vary from implementation to implementation depending upon numerous factors, such as price constraints, performance requirements, technological improvements, or other circumstances. Examples of the electronic device or computer system 400 may include without limitation a mobile device, a personal digital assistant, a mobile computing device, a smartphone, a cellular telephone, a handset, a one-way pager, a two-way pager, a messaging device, a computer, a personal computer (PC), a desktop computer, a laptop computer, a notebook computer, a handheld computer, a tablet computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, television, digital television, set top box, wireless access point, base station, subscriber station, mobile subscriber center, radio network controller, router, hub, gateway, bridge, switch, machine, or combinations thereof.

Embodiments may be implemented as any or a combination of: one or more microchips or integrated circuits interconnected using a parentboard, hardwired logic, software stored by a memory device and executed by a microprocessor, firmware, an application specific integrated circuit (ASIC), and/or a field programmable gate array (FPGA). The term "logic" may include, by way of example, software or hardware and/or combinations of software and hardware.

Embodiments may be provided, for example, as a computer program product which may include one or more machine-readable media having stored thereon machine-executable instructions that, when executed by one or more machines such as a computer, network of computers, or other electronic devices, may result in the one or more machines carrying out operations in accordance with embodiments described herein. A machine-readable medium may include, but is not limited to, floppy diskettes, optical disks, CD-ROMs (Compact Disc-Read Only Memories), and magneto-optical disks, ROMs, RAMs, EPROMs (Erasable Programmable Read Only Memories), EEPROMs (Electrically Erasable Programmable Read Only Memories), magnetic or optical cards, flash memory, or other type of media/machine-readable medium suitable for storing machine-executable instructions.

Moreover, embodiments may be downloaded as a computer program product, wherein the program may be transferred from a remote computer (e.g., a server) to a requesting computer (e.g., a client) by way of one or more data signals embodied in and/or modulated by a carrier wave or other propagation medium via a communication link (e.g., a modem and/or network connection).

References to "one embodiment", "an embodiment", "example embodiment", "various embodiments", etc., indicate that the embodiment(s) so described may include particular features, structures, or characteristics, but not every embodiment necessarily includes the particular features, structures, or characteristics. Further, some embodiments may have some, all, or none of the features described for other embodiments.

In the following description and claims, the term "coupled" along with its derivatives, may be used. "Coupled" is used to indicate that two or more elements co-operate or interact with each other, but they may or may not have intervening physical or electrical components between them.

As used in the claims, unless otherwise specified the use of the ordinal adjectives "first", "second", "third", etc., to describe a common element, merely indicate that different instances of like elements are being referred to, and are not intended to imply that the elements so described must be in a given sequence, either temporally, spatially, in ranking, or in any other manner.

The following clauses and/or examples pertain to further embodiments or examples. Specifics in the examples may be used anywhere in one or more embodiments. The various features of the different embodiments or examples may be variously combined with some features included and others excluded to suit a variety of different applications. Examples may include subject matter such as a method, means for performing acts of the method, at least one machine-readable medium including instructions that, when performed by a machine cause the machine to performs acts of the method, or of an apparatus or system for facilitating hybrid communication according to embodiments and examples described herein.

Some embodiments pertain to Example 1 that includes an apparatus to facilitating eye torsion-based accurate eye tracking on computing devices, comprising: head pose estimation logic to determine a head pose representing a tilt of a head of a person in an image captured by a capturing device of one or more capturing/sensing device, wherein the image illustrates one or more eyes of the person; gravity vector estimation logic to estimate a gravity vector relating to an eye of the one or more eyes based on data relating to the image and sensed by a sensing device of the one or more capturing/sensing devices; torsion estimation logic to compute a total torsion angle based on one or more of the head pose and the gravity vector; and gaze vector estimation logic to estimate a gaze vector associated with eye to facilitate tracking of the eye, wherein tracking includes positions or movements of the eye based on the gaze vector.

Example 2 includes the subject matter of Example 1, further comprising reception/detection logic to receive the image and the sensed data from the capturing device and the sensing device, respectively, wherein the capturing device comprises a camera, and wherein the sensing device comprises an accelerometer.

Example 3 includes the subject matter of Example 1, further comprising eye tracking computation logic to compute one or more axes of the eyes, wherein the one or more axes includes an optical axis relating to the eye, wherein the optical axis is used to compute a visual axis relating to the eye.

Example 4 includes the subject matter of Example 1, wherein the gaze vector is estimated based on one or more of the optical axis, visual axis, and the total torsion angle.

Example 5 includes the subject matter of Example 1, wherein the estimation of the torsion angle is further based on a first torsion angle and a second torsion angle, wherein the first torsion angle includes a Listing's torsion angle, and a second torsion angle includes a tilt torsion angle.

Example 6 includes the subject matter of Example 5, wherein the tilt torsion angle corresponds to the head pose representing the tilt of the head of the person in the image, wherein the tilt of the head corresponds to one or more degrees of freedom associated with one or more orientations of the head, wherein the one or more degrees of freedom include one or more of a roll, a pitch, and a yaw, wherein the image includes a three-dimensional ("3D") image.

Example 7 includes the subject matter of Example 5, wherein the tilt torsion angle is measured at least in part based on a relationship between a first torsion angle and a second torsion angle, wherein the first torsion angle includes a gravity vector that is constant, and the second torsion vector includes an eye-to-eye vector that is dynamically changing.

Example 8 includes the subject matter of Example 1, further comprising features extraction and evaluation logic to extract one or more features relating to the eye, wherein the one or more features include locations of one or more of an eyeball, a cornea, a fovea, and a center of the eye, wherein the optical axis is determined based on the one or more features.

Some embodiments pertain to Example 9 that includes a method for facilitating eye torsion-based accurate eye tracking on computing devices, comprising: determining a head pose representing a tilt of a head of a person in an image captured by a capturing device of one or more capturing/sensing device, wherein the image illustrates one or more eyes of the person; estimating a gravity vector relating to an eye of the one or more eyes based on data relating to the image and sensed by a sensing device of the one or more capturing/sensing devices; computing a total torsion angle based on one or more of the head pose and the gravity vector; and estimating a gaze vector associated with eye to facilitate tracking of the eye, wherein tracking includes positions or movements of the eye based on the gaze vector.

Example 10 includes the subject matter of Example 9, further comprising receiving the image and the sensed data from the capturing device and the sensing device, respectively, wherein the capturing device comprises a camera, and wherein the sensing device comprises an accelerometer.

Example 11 includes the subject matter of Example 9, further comprising computing one or more axes of the eyes, wherein the one or more axes includes an optical axis relating to the eye, wherein the optical axis is used to compute a visual axis relating to the eye.

Example 12 includes the subject matter of Example 9, wherein the gaze vector is estimated based on one or more of the optical axis, visual axis, and the total torsion angle.

Example 13 includes the subject matter of Example 9, wherein the computation of the torsion angle is further based on a first torsion angle and a second torsion angle, wherein the first torsion angle includes a Listing's torsion angle, and a second torsion angle includes a tilt torsion angle.

Example 14 includes the subject matter of Example 13, wherein the tilt torsion angle corresponds to the head pose representing the tilt of the head of the person in the image, wherein the tilt of the head corresponds to one or more degrees of freedom associated with one or more orientations of the head, wherein the one or more degrees of freedom include one or more of a roll, a pitch, and a yaw, wherein the image includes a three-dimensional ("3D") image.

Example 15 includes the subject matter of Example 13, wherein the tilt torsion angle is measured at least in part based on a relationship between a first torsion angle and a second torsion angle, wherein the first torsion angle includes a gravity vector that is constant, and the second torsion vector includes an eye-to-eye vector that is dynamically changing.

Example 16 includes the subject matter of Example 9, further comprising extracting one or more features relating to the eye, wherein the one or more features include locations of one or more of an eyeball, a cornea, a fovea, and a center of the eye, wherein the optical axis is determined based on the one or more features.

Example 17 includes at least one machine-readable medium comprising a plurality of instructions, when executed on a computing device, to implement or perform a method or realize an apparatus as claimed in any preceding claims.

Example 18 includes at least one non-transitory or tangible machine-readable medium comprising a plurality of instructions, when executed on a computing device, to implement or perform a method or realize an apparatus as claimed in any preceding claims.

Example 19 includes a system comprising a mechanism to implement or perform a method or realize an apparatus as claimed in any preceding claims.

Example 20 includes an apparatus comprising means to perform a method as claimed in any preceding claims.

Example 21 includes a computing device arranged to implement or perform a method or realize an apparatus as claimed in any preceding claims.

Example 22 includes a communications device arranged to implement or perform a method or realize an apparatus as claimed in any preceding claims.

Some embodiments pertain to Example 23 includes a system comprising a storage device having instructions, and a processor to execute the instructions to facilitate a mechanism to perform one or more operations comprising: determining a head pose representing a tilt of a head of a person in an image captured by a capturing device of one or more capturing/sensing device, wherein the image illustrates one or more eyes of the person; estimating a gravity vector relating to an eye of the one or more eyes based on data relating to the image and sensed by a sensing device of the one or more capturing/sensing devices; computing a total torsion angle based on one or more of the head pose and the gravity vector; and estimating a gaze vector associated with eye to facilitate tracking of the eye, wherein tracking includes positions or movements of the eye based on the gaze vector.

Example 24 includes the subject matter of Example 23, wherein the one or more operations comprise receiving the image and the sensed data from the capturing device and the sensing device, respectively, wherein the capturing device comprises a camera, and wherein the sensing device comprises an accelerometer.

Example 25 includes the subject matter of Example 23, wherein the one or more operations comprise computing one or more axes of the eyes, wherein the one or more axes includes an optical axis relating to the eye, wherein the optical axis is used to compute a visual axis relating to the eye.

Example 26 includes the subject matter of Example 23, wherein the gaze vector is estimated based on one or more of the optical axis, visual axis, and the total torsion angle.

Example 27 includes the subject matter of Example 23, wherein the computation of the torsion angle is further based on a first torsion angle and a second torsion angle, wherein the first torsion angle includes a Listing's torsion angle, and a second torsion angle includes a tilt torsion angle.

Example 28 includes the subject matter of Example 27, wherein the tilt torsion angle corresponds to the head pose representing the tilt of the head of the person in the image, wherein the tilt of the head corresponds to one or more degrees of freedom associated with one or more orientations of the head, wherein the one or more degrees of freedom include one or more of a roll, a pitch, and a yaw, wherein the image includes a three-dimensional ("3D") image.

Example 29 includes the subject matter of Example 27, wherein the tilt torsion angle is measured at least in part based on a relationship between a first torsion angle and a second torsion angle, wherein the first torsion angle includes a gravity vector that is constant, and the second torsion vector includes an eye-to-eye vector that is dynamically changing.

Example 30 includes the subject matter of Example 23, wherein the one or more operations comprise extracting one or more features relating to the eye, wherein the one or more features include locations of one or more of an eyeball, a cornea, a fovea, and a center of the eye, wherein the optical axis is determined based on the one or more features.

Some embodiments pertain to Example 31 includes an apparatus comprising: means for determining a head pose representing a tilt of a head of a person in an image captured by a capturing device of one or more capturing/sensing device, wherein the image illustrates one or more eyes of the person; means for estimating a gravity vector relating to an eye of the one or more eyes based on data relating to the image and sensed by a sensing device of the one or more capturing/sensing devices; means for computing a total torsion angle based on one or more of the head pose and the gravity vector; and means for estimating a gaze vector associated with eye to facilitate tracking of the eye, wherein tracking includes positions or movements of the eye based on the gaze vector.

Example 32 includes the subject matter of Example 31, further comprising means for receiving the image and the sensed data from the capturing device and the sensing device, respectively, wherein the capturing device comprises a camera, and wherein the sensing device comprises an accelerometer.

Example 33 includes the subject matter of Example 31, further comprising means for computing one or more axes of the eyes, wherein the one or more axes includes an optical axis relating to the eye, wherein the optical axis is used to compute a visual axis relating to the eye.

Example 34 includes the subject matter of Example 31, wherein the gaze vector is estimated based on one or more of the optical axis, visual axis, and the total torsion angle.

Example 35 includes the subject matter of Example 31, wherein the computation of the torsion angle is further based on a first torsion angle and a second torsion angle, wherein the first torsion angle includes a Listing's torsion angle, and a second torsion angle includes a tilt torsion angle.

Example 36 includes the subject matter of Example 35, wherein the tilt torsion angle corresponds to the head pose representing the tilt of the head of the person in the image, wherein the tilt of the head corresponds to one or more degrees of freedom associated with one or more orientations of the head, wherein the one or more degrees of freedom include one or more of a roll, a pitch, and a yaw, wherein the image includes a three-dimensional ("3D") image.

Example 37 includes the subject matter of Example 35, wherein the tilt torsion angle is measured at least in part based on a relationship between a first torsion angle and a second torsion angle, wherein the first torsion angle includes a gravity vector that is constant, and the second torsion vector includes an eye-to-eye vector that is dynamically changing.

Example 38 includes the subject matter of Example 31, wherein the one or more operations comprise extracting one or more features relating to the eye, wherein the one or more features include locations of one or more of an eyeball, a cornea, a fovea, and a center of the eye, wherein the optical axis is determined based on the one or more features.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

What is claimed is:

1. An apparatus comprising:
   a processing device coupled to memory, wherein the processing device configured to facilitate:
   head pose estimation logic to determine head orientation of a head of a person in relation to one or more eyes of the person and further in relation to a world reference frame as determined based on orientation of a capturing device, wherein the head orientation further includes a head pose representing a tilt of the head of the person in an image captured by the capturing device of one or more capturing/sensing devices, wherein the image illustrates the one or more eyes of the person;
   gravity vector estimation logic to estimate a gravity vector relating to an eye of the one or more eyes based on data relating to the image and sensed by a sensing device of the one or more capturing/sensing devices;
   torsion estimation logic to compute a total torsion angle based on one or more of the head pose and the gravity vector in a vertical plane containing the gravity vector and an eye of the one or more eyes, wherein the head pose is based one or more degrees of freedom, wherein a degree of freedom includes torsional rotation including spontaneous controlling when a gaze point is changed, and compensating for the head tilt where the one or more eyes keep their orientation relating to a gravitational horizon of the earth, wherein the total torsion angle relates to torsional rotation that is controlled through a first motion relating to spontaneous changing of a gaze vector or a second motion relating to movement compensation associated with the head tilt; and
   gaze vector estimation logic to estimate the gaze vector associated with the eye to facilitate tracking of the eye, wherein tracking includes positions or movements of the eye based on the gaze vector referring to a gaze direction, and the gaze point referring to a point of intersection of the gaze vector and a screen, wherein the gaze vector is further estimated based on an optical axis or a visual axis of the eye, wherein the optical axis relates to a first line that passes through a center of curvature of a cornea of the eye and runs parallel to an axis of symmetry, wherein the visual axis relates to a second line that passes through a nodal point of the eye.

2. The apparatus of claim 1, wherein the processing device is further configured to facilitate reception/detection logic to receive the image and the sensed data from the capturing device and the sensing device, respectively, wherein the capturing device comprises a camera, and wherein the sensing device comprises an accelerometer.

3. The apparatus of claim 1, wherein the processing device is further configured to facilitate eye tracking computation logic to compute one or more axes of the eyes, wherein the one or more axes includes the optical axis relating to the eye, wherein the optical axis is used to compute the visual axis relating to the eye.

4. The apparatus of claim 1, wherein the gaze vector is estimated based on one or more of the optical axis, the visual axis, and the total torsion angle.

5. The apparatus of claim 1, wherein the estimation of the torsion angle is further based on a first torsion angle and a second torsion angle, wherein the first torsion angle includes a Listing's torsion angle, and a second torsion angle includes a tilt torsion angle.

6. The apparatus of claim 5, wherein the tilt torsion angle corresponds to the head pose representing the tilt of the head of the person in the image, wherein the tilt of the head corresponds to the one or more degrees of freedom associated with one or more orientations of the head, wherein the one or more degrees of freedom include one or more of a roll, a pitch, and a yaw, wherein the image includes a three-dimensional ("3D") image.

7. The apparatus of claim 5, wherein the tilt torsion angle is measured at least in part based on a relationship between a first torsion vector and a second torsion vector, wherein the first torsion vector includes a gravity vector that is constant, and the second torsion vector includes an eye-to-eye vector that is dynamically changing.

8. The apparatus of claim 1, wherein the processing device is further configured to facilitate features extraction and evaluation logic to extract one or more features relating to the eye, wherein the one or more features include locations of one or more of an eyeball, a cornea, a fovea, and a center of the eye, wherein the optical axis is determined based on the one or more features.

9. A method comprising:
   determining head orientation of a head of a person in relation to one or more eyes of the person and further in relation to a world reference frame as determined based on orientation of a capturing device, wherein the head orientation further includes a head pose representing a tilt of the head of the person in an image captured by the capturing device of one or more capturing/sensing devices, wherein the image illustrates the one or more eyes of the person;
   estimating a gravity vector relating to an eye of the one or more eyes based on data relating to the image and sensed by a sensing device of the one or more capturing/sensing devices;
   computing a total torsion angle based on one or more of the head pose and the gravity vector in a vertical plane containing the gravity vector and an eye of the one or more eyes, wherein the head pose is based one or more degrees of freedom, wherein a degree of freedom includes torsional rotation including spontaneous controlling when a gaze point is changed, and compensating for the head tilt where the one or more eyes keep their orientation relating to a gravitational horizon of the earth, wherein the total torsion angle relates to torsional rotation that is controlled through a first motion relating to spontaneous changing of a gaze vector or a second motion relating to movement compensation associated with the head tilt; and
   estimating the gaze vector associated with the eye to facilitate tracking of the eye, wherein tracking includes positions or movements of the eye based on the gaze vector referring to a gaze direction, and the gaze point referring to a point of intersection of the gaze vector and a screen, wherein the gaze vector is further estimated based on an optical axis or a visual axis of the eye, wherein the optical axis relates to a first line that passes through a center of curvature of a cornea of the eye and runs parallel to an axis of symmetry, wherein the visual axis relates to a second line that passes through a nodal point of the eye.

10. The method of claim 9, further comprising receiving the image and the sensed data from the capturing device and the sensing device, respectively, wherein the capturing device comprises a camera, and wherein the sensing device comprises an accelerometer.

11. The method of claim 9, further comprising computing one or more axes of the eyes, wherein the one or more axes includes the optical axis relating to the eye, wherein the optical axis is used to compute the visual axis relating to the eye.

12. The method of claim 9, wherein the gaze vector is estimated based on one or more of the optical axis, the visual axis, and the total torsion angle.

13. The method of claim 9, wherein the computation of the torsion angle is further based on a first torsion angle and a second torsion angle, wherein the first torsion angle includes a Listing's torsion angle, and a second torsion angle includes a tilt torsion angle.

14. The method of claim 13, wherein the tilt torsion angle corresponds to the head pose representing the tilt of the head of the person in the image, wherein the tilt of the head corresponds to the one or more degrees of freedom associated with one or more orientations of the head, wherein the one or more degrees of freedom include one or more of a roll, a pitch, and a yaw, wherein the image includes a three-dimensional ("3D") image.

15. The method of claim 13, wherein the tilt torsion angle is measured at least in part based on a relationship between a first torsion vector and a second torsion vector, wherein the first torsion vector includes a gravity vector that is constant, and the second torsion vector includes an eye-to-eye vector that is dynamically changing.

16. The method of claim 9, further comprising extracting one or more features relating to the eye, wherein the one or more features include locations of one or more of an eyeball, a cornea, a fovea, and a center of the eye, wherein the optical axis is determined based on the one or more features.

17. At least one non-transitory machine-readable medium comprising a plurality of instructions, executed on a computing device, to facilitate the computing device to perform one or more operations comprising:
   determining head orientation of a head of a person in relation to one or more eyes of the person and further in relation to a world reference frame as determined based on orientation of a capturing device, wherein the head orientation further includes a head pose representing a tilt of the head of the person in an image captured by a capturing device of one or more capturing/sensing device, wherein the image illustrates one or more eyes of the person;

estimating a gravity vector relating to an eye of the one or more eyes based on data relating to the image and sensed by a sensing device of the one or more capturing/sensing devices;

computing a total torsion angle based on one or more of the head pose and the gravity vector in a vertical plane containing the gravity vector and an eye of the one or more eyes, wherein the head pose is based one or more degrees of freedom, wherein a degree of freedom includes torsional rotation including spontaneous controlling when a gaze point is changed, and compensating for the head tilt where the one or more eyes keep their orientation relating to a gravitational horizon of the earth, wherein the total torsion angle relates to torsional rotation that is controlled through a first motion relating to spontaneous changing of a gaze vector or a second motion relating to movement compensation associated with the head tilt; and estimating the gaze vector associated with the eye to facilitate tracking of the eye, wherein tracking includes positions or movements of the eye based on the gaze vector referring to a gaze direction, and the gaze point referring to a point of intersection of the gaze vector and a screen, wherein the gaze vector is further estimated based on an optical axis or a visual axis of the eye, wherein the optical axis relates to a first line that passes through a center of curvature of a cornea of the eye and runs parallel to an axis of symmetry, wherein the visual axis relates to a second line that passes through a nodal point of the eye.

18. The non-transitory machine-readable medium of claim 17, wherein the one or more operations comprising receiving the image and the sensed data from the capturing device and the sensing device, respectively, wherein the capturing device comprises a camera, and wherein the sensing device comprises an accelerometer.

19. The non-transitory machine-readable medium of claim 17, wherein the one or more operations comprising computing one or more axes of the eyes, wherein the one or more axes includes the optical axis relating to the eye, wherein the optical axis is used to compute the visual axis relating to the eye.

20. The non-transitory machine-readable medium of claim 17, wherein the gaze vector is estimated based on one or more of the optical axis, the visual axis, and the total torsion angle.

21. The non-transitory machine-readable medium of claim 17, wherein the computation of the torsion angle is further based on a first torsion angle and a second torsion angle, wherein the first torsion angle includes a Listing's torsion angle, and a second torsion angle includes a tilt torsion angle.

22. The non-transitory machine-readable medium of claim 21, wherein the tilt torsion angle corresponds to the head pose representing the tilt of the head of the person in the image, wherein the tilt of the head corresponds to the one or more degrees of freedom associated with one or more orientations of the head, wherein the one or more degrees of freedom include one or more of a roll, a pitch, and a yaw, wherein the image includes a three-dimensional ("3D") image.

23. The non-transitory machine-readable medium of claim 21, wherein the tilt torsion angle is measured at least in part based on a relationship between a first torsion vector and a second torsion vector, wherein the first torsion vector includes a gravity vector that is constant, and the second torsion vector includes an eye-to-eye vector that is dynamically changing.

24. The non-transitory machine-readable medium of claim 17, wherein the one or more operations comprising extracting one or more features relating to the eye, wherein the one or more features include locations of one or more of an eyeball, a cornea, a fovea, and a center of the eye, wherein the optical axis is determined based on the one or more features.

* * * * *